Figure 1:
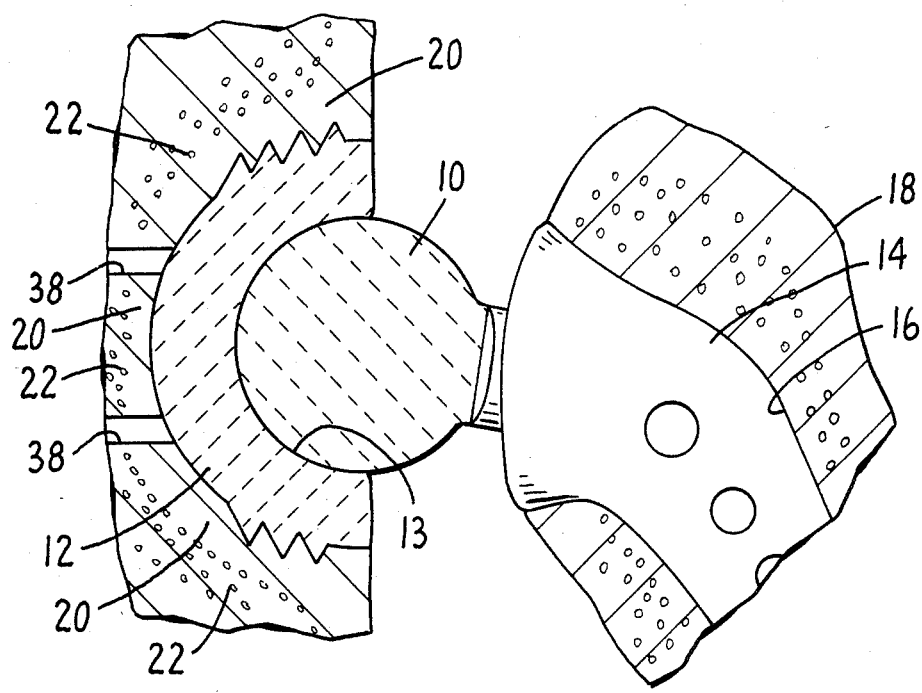

United States Patent [19]
Powlan

[11] Patent Number: 4,802,468
[45] Date of Patent: * Feb. 7, 1989

[54] DEVICE FOR CUTTING THREADS IN THE WALLS OF THE ACETABULAR CAVITY IN HUMANS

[76] Inventor: Roy Y. Powlan, 1 Chapel Dr., Lafayette, Calif. 94549

[*] Notice: The portion of the term of this patent subsequent to Sep. 16, 2003 has been disclaimed.

[21] Appl. No.: 899,162

[22] Filed: Aug. 22, 1986

Related U.S. Application Data

[63] Continuation-in-part of Ser. No. 653,096, Sep. 24, 1984, Pat. No. 4,611,587.

[51] Int. Cl.⁴ .............................................. A61F 5/04
[52] U.S. Cl. ............................ 128/92 V; 128/92 VJ; 128/92 YF
[58] Field of Search ........... 128/92 V, 92 VS, 92 YF, 128/92 VV

[56] References Cited

U.S. PATENT DOCUMENTS

| | | | |
|---|---|---|---|
| 4,262,369 | 4/1981 | Roux | 128/92 YF |
| 4,271,849 | 6/1981 | Rehder | 128/92 V |
| 4,273,117 | 6/1981 | Neuhäuser | 128/92 V |
| 4,611,587 | 9/1986 | Powlan | 128/92 VJ |
| 4,621,637 | 11/1986 | Fishbein | 128/92 V |
| 4,662,891 | 5/1987 | Nailes | 128/92 VV |

OTHER PUBLICATIONS

J. of Bone & Joint Surg., 6/84, vol. 66-A, pp. 44–49, 54–55, 59–67, 72–74, 79–80, 100, 123.
Richards, "The AUTOPHOR TM Cementless Ceramic Hip System Operative Technique" by Edward A. Miller, pre 1984.

*Primary Examiner*—C. Fred Rosenbaum
*Assistant Examiner*—Colleen Reilly
*Attorney, Agent, or Firm*—John R. Murtha

[57] ABSTRACT

The invention relates to total hip joint replacements in humans in which the ball-like head of the femur and the cup-shaped cavity of the acetabulum are replaced by metal, plastic or ceramic substitutes and, more particularly, to a device for cutting screw threads in the wall of the acetabulum to receive a threaded substitute hip socket.

6 Claims, 2 Drawing Sheets

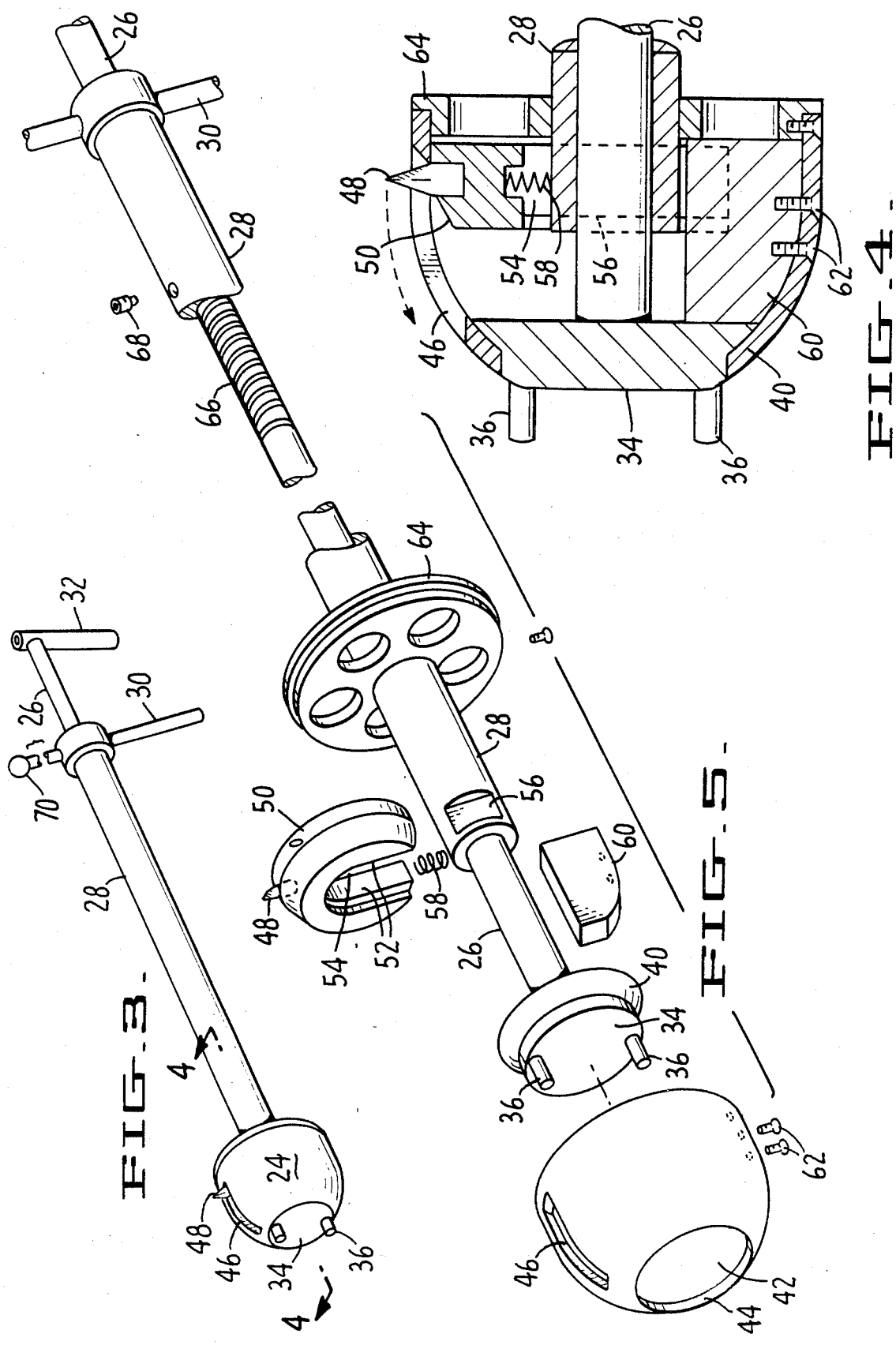

DEVICE FOR CUTTING THREADS IN THE WALLS OF THE ACETABULAR CAVITY IN HUMANS

The invention relates to total hip joint replacement in humans in which the ball-like head of the femur and the cupshaped cavity of the acetabulum are replaced by metal, plastic or ceramic substitutes and, more particularly, to a device for cutting screw threads in the walls of the acetabulum to receive a threaded substitute hip socket. This application is a continuation-in-part application of my earlier application, now U.S. Pat. No. 4,611,587 filed Sept. 24, 1984.

Since the later 1960's it has been customary to utilize a plastic cement to fixedly secure the substitute hip components employed in total hip joint replacement surgery. It has been found, however, that this method of fixing the components into the patient's surrounding bone has serious drawbacks because the cement often becomes brittle and cracks after being in place a few years. As a result the substitute components loosen and migrate from their proper positions thereby causing both pain and deformity and necessitating further corrective surgery.

To avoid these problems it is now preferred to utilize other methods of attaching the substitute hip components to the patient. A frequently used method for fixing the acetabular component into the hip bone socket cavity, the acetabulum, is to form screw threads on the outer surface of the acetabular component so that it can be screwed directly into the previously prepared acetabulum. The exterior shape of the substitute acetabular components currently available vary considerably, but generally are hemispherical, truncated cones or cylinders, with screw threads of various size, shape and pitch formed on their outer surfaces. Preparation of the acetabulum is accomplished by chiseling, reaming or scraping the interior of the roughly hemispherical hip socket cavity to remove cartilage and some or all of the bony wall until the acetabulum is modified to substantially conform to the size and shape of the acetabular component that will be fitted into it. While some acetabular components have self-tapping threads on their exterior surfaces to permit the component to be screwed directly into the prepared acetabulum, other components require that the bony wall be threaded with a tapping device before the acetabular component can be inserted into the hip socket cavity.

As presently done, this threading operation is carried out using a hand tap or plug having the same size and shape as the prepared acetabulum with cutting threads affixed to the plug's external surface. The use of a conical hand tap requires that the threads be cut simultaneously around the wall of the acetabulum, a very difficult task that requires a great deal of physical force. Indeed, despite great force, it is difficult to cut full depth threads into the relatively hard cortical layer of bone which lines most of the acetabulum. The force of turning the conical tap into the bony wall can cause expansive strains on the walls of the acetabulum causing it to fracture and prevent mechanical fixation of the component. In addition, if the threads are not of fully depth and of the proper size and shape, the threaded acetabular component will not seat in the socket properly or deeply enough. Accordingly, it is customary in preparing the acetabulum to cut away most of this hard cortical outer layer of bone in the chiseling and reaming operation to expose the much softer and spongy cancellous bone beneath it. Although it is much easier to create screw threads in this softer cancellous bone it does not provide as strong a supporting medium for anchoring the acetabular component as the hard cortical layer and the risk that the component will loosen in time is much greater.

The objective of the present invention is to provide a device for cutting threads in the acetabulum that does not have the drawbacks and disadvantages discussed above. Another object of the invention is to provide a tool that will enable threads to be easily cut in the hard cortical layer of the acetabular cavity.

Still another object of the invention is to provide a tool whose cutting head can be readily modified to match the contours of a bony hip socket that has been reamed and shaped to conform to the size and shape of a substitute acetabular component.

Figure 2:
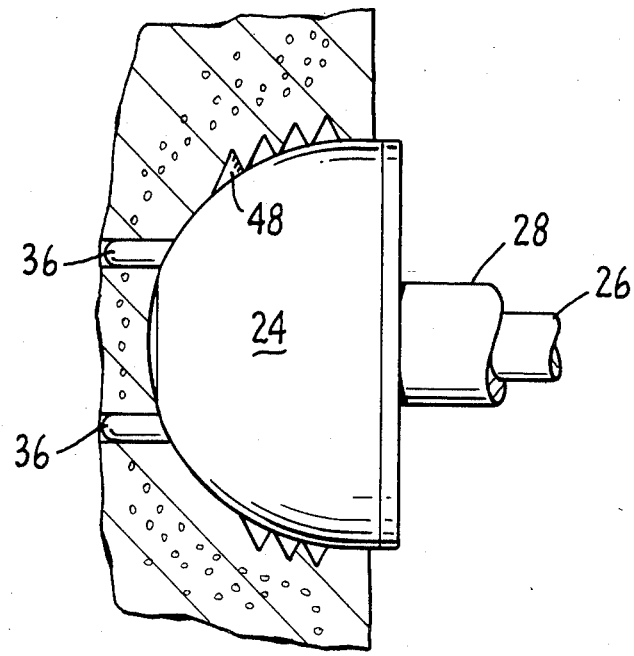
Figure 6:
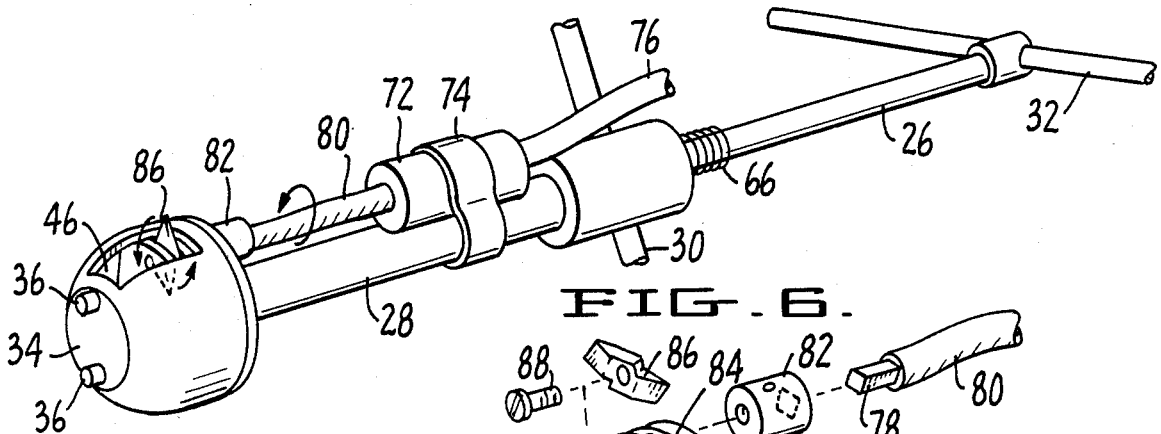
Figure 7:
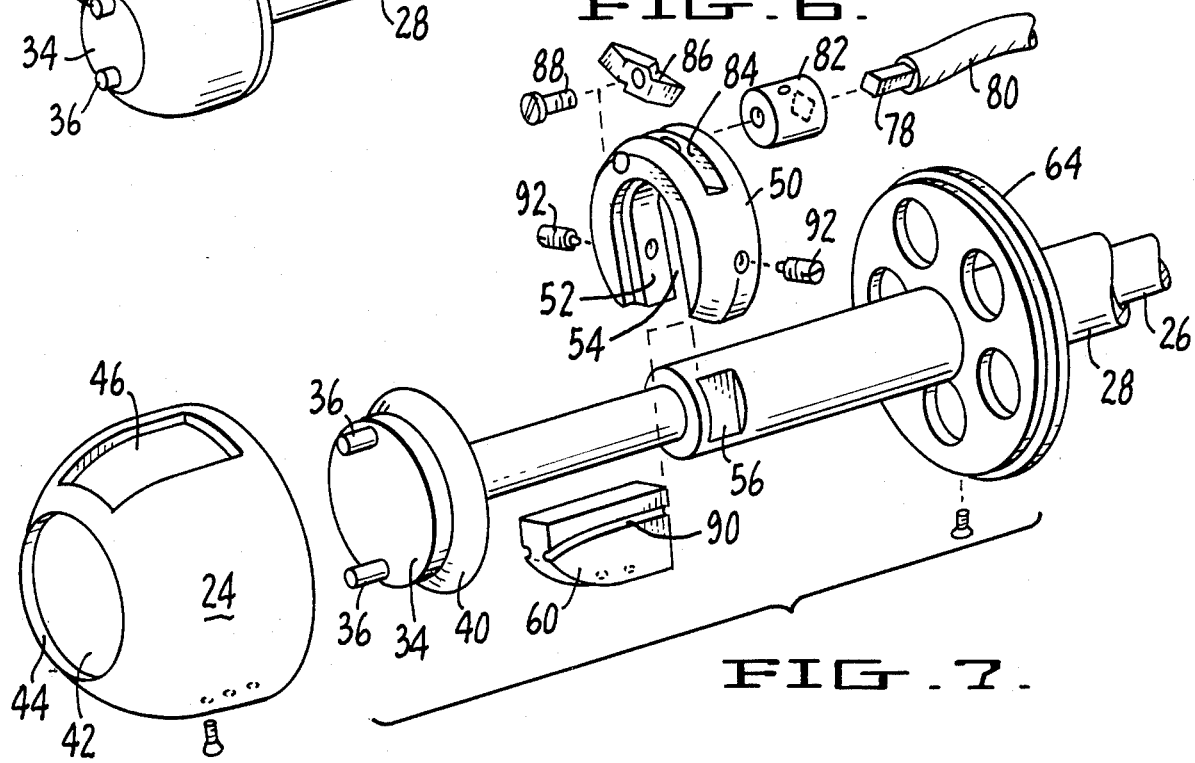
Figure 8:
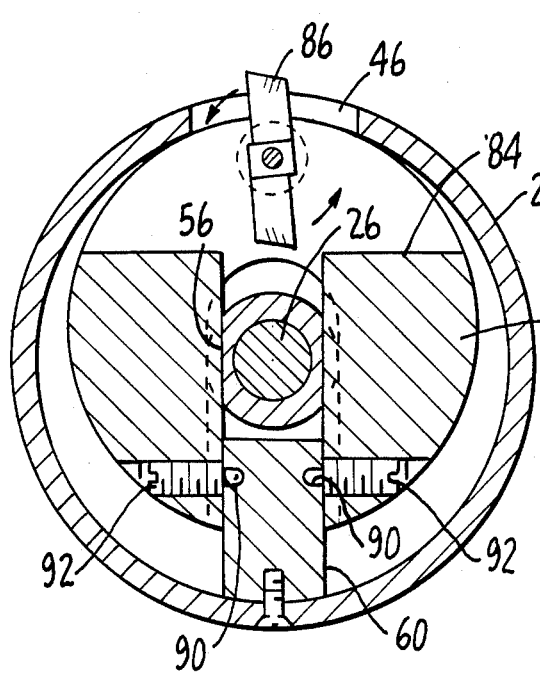
Figure 9:
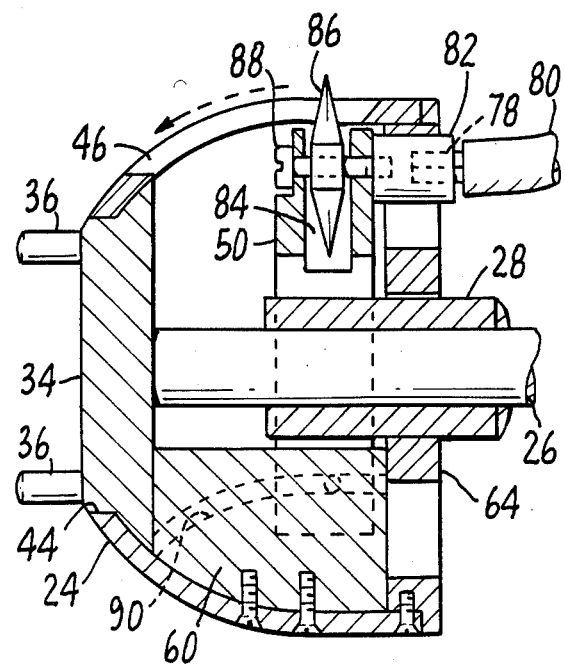

In the accompanying drawings, in which similar reference numerals refer to similar parts, FIG. 1 is a sectional view showing the placement of the substitute components in a total hip joint replacement, FIG. 2 is a sectional view showing the head of applicant's device cutting threads in the hard, bony cortical wall of the acetabulum, FIG. 3 is a perspective view of applicant's tool, FIG. 4 is a sectional view through the head of applicant's tool, taken along the line 4—4 in FIG. 3, looking in the direction of the arrows, FIG. 5 is an exploded view of applicant's tool, FIG. 6 is a perspective view of a modified form of the invention in which the cutting tool is driven by an air motor, FIG. 7 is an exploded view of the modified form of applicant's invention, FIG. 8 is a transverse sectional view of the cutting head, and FIG. 9 is a longitudinal sectional view of the cutting head.

In the course of a total hip joint replacement, the ball-like head on the femur is replaced by a substitute metal, plastic or ceramic head. Because the bony hip socket or acetabulum is often diseased or deformed, the socket is also replaced by an acetabular component composed of the same or complimentary materials or a combination of them. A presently available set of such substitutes are shown in FIG. 1. As will be seen there, the substitute femoral head 10 and acetabular cup 12, with a head-matching hemispherical socket 13, are formed from a high strength, super-hard ceramic while the substitute femoral stem 14 is formed from a cobalt-chromium-molybdenum cast alloy. The stem of the femoral head 14 is inserted into the medullary canal 16 of the femur 18 and locked there in accord with presently known procedures that do not concern us since the present invention relates to the placement of the acetabular cup. While the specific materials used in the substitute components shown in the drawing have been identified, it is to be understood that there is nothing critical about them and that other constituent materials could be used just as well. In addition, the materials used could be coated with a porous coating commonly used to assist in the fixation of the component to the bone since bone cells will grow into the pores of the coating.

The acetabular cavity that forms the socket for a normal, healthy hip joint is roughly hemispherical but not perfectly so. Furthermore, the roughly hemispherical shape can be greatly modified by diseases of the hip joint. For the most part, the walls of the acetabular cavity are formed by a hard, bony shell of varying thickness called the cortical layer 20. This fairly thin layer of hard, bony shell is supported from its under surface by the softer, spongy cancellous bone 22 of the pelvis. Unlike the prior art procedures, applicant's device requires little preparation of the acetabulum. The superficial cartilage surface of the acetabulum is removed, but depending on the exact external configuration of the acetabular component to be inserted, it is not necessary to remove the hard, bony cortical layer 20 of the hip socket's wall or bottom.

The applicant's thread cutting device comprises a hand tool having a cutting head 24 shaped to closely match and configuration of the acetabular component to be inserted. Since the cutting head is matched to the acetabular component it is important that the acetabular component be of a shape that closely fits the particular shape of the patient's acetabulum so that the cutting head will, in turn, closely match the size and shape of the hip socket cavity being replaced. When this relationship is maintained, the external shape of the cutting head 24 will closely conform to the patient's acetabulum and serve to keep the tool centered in the acetabulum while the threads are being cut in the walls of the socket and the threads will be of a uniform depth and shape. If the relationship is not maintained there will be a poor fit between the tool and the acetabulum and the tool will be able to wobble or otherwise wander during the cutting of the threads with the result that the threads will have non-uniform shape and depth.

A central shaft 26 is enclosed within an independently rotatable drive shaft 28 for the cutting head, and a pair of of handles 30,32 control the operation of the device. As is best seen in FIG. 5, the central shaft 26 extends throughout the length of the device. At its forward end the central shaft 26 is fixed to a generally cylindrical alignment disk 34 that carries two axially disposed, parallel pegs 36,36 adapted to fit within two similarly sized locating holes 38,38 drilled in the bottom of the patient's acetabulum. Immediately behind the locating pegs 36,36 the alignment disk 34 has an arcuate flange 40 shaped to the inner curvature of the cutting head 24. The function of this flange 40 is to position the alignment disk 34 in sliding engagement with the cutting head 24 so as to position and maintain the head at the forward end of the central shaft 26 while still permitting rotation of the head relative to the shaft.

For this reasons previously described, the cutting head 24 has substantially the same shape as the threaded acetabular cup that will be permanently secured in the patient's hip socket. In general, this shape will be nearly hemispherical, although cutting heads in a number of different shapes and sizes are necessary in order to accommodate a full range of variations in patient's hip socket cavities. At its forward end, the cutting head has a circular opening 42 to accommodate the alignment disk 34 and the side walls 44 of the opening 42 in the head are sized so that the head fits closely about the disk 34 and is aligned therewith. The head 24 is also formed with an elongated, axial slot 46 through which the cutting tool bit 48 protrudes as will be described in more detail hereafter.

A tool carrier 50, with the cutting tool bit 48 fixedly mounted therein, is adapted for connection with the drive shaft 28 in a manner that will cause the cutting tool bit to rotate with the shaft yet be radially slidable with respect thereto. To this end the tool carrier 50 is formed like the letter "C", that is, in a generally annular configuration but one that is not a complete circle. The inner surface 52,52 of the central opening 54 in the tool carrier 50 are straight and parallel and correspondingly shaped slots 56,56 are formed in the forward end of the drive shaft 28 to permit the carrier to move outwardly of the shaft. A coil spring 58 between the carrier 50 and the shaft 28 continuously biases the tool carrier toward the inner surface of the cutting head so that the cutting tool bit 48 is always positioned to cut to the proper depth in the side wall while following the profile of the cavity's walls. In the assembled position of applicant's tool shown in FIG. 4, the inner surfaces 52,52 of the central opening 54 in the tool carrier 50 also straddle a drive block 60 that is fixedly mounted by screws 62,62 to the inner surface of the cutting head 24. This arrangement operates to transfer the rotational motion of the drive shaft into rotation of the cutting head and cutting tool bit. The drive block 60 also serves to hold the alignment disk 34 locked into position in the circular opening 42 of the cutting head 24. An end plate 64 closes off the outer end of the cutting head 24 and maintains the drive shaft 28 in it's central location.

The outer drive shaft 28 surrounds the inner central shaft 26 and is rotatable with respect to it. Rotation of the drive shaft 28 occurs when the double handle 30 at the end of the tool is rotated. A lead screw 66 is formed intermediate the ends of the central shaft 26 and a pair of oppositely disposed thread followers 68,68 (only one of which is shown) are carried by the drive shaft 28. Rotation of the drive shaft relative to the central shaft accordingly causes the drive shaft to slide longitudinally along the central shaft. This helical rotation of the drive shaft causes the cutting tool bit 48 in the head 24 to rotate helically and cut threads into the hard, bony shell of the acetabular cavity. A knob 70 is provided on one end of the double handle 30 and this knob is preferably lined up with the cutting tool 48 so that the position of the knob 70 indicates to the surgeon exactly where the cutting tool is working. While the handle 30 operating the drive shaft is being rotated, the handle 32 on the central shaft 26 is held steady so that the tool, having been oriented by the two location holes in the bottom of the acetabulum, is maintained in that orientation. The single handle 32 on this shaft is preferably lined up with the two locating pegs 36,36 so that the surgeon may easily keep track of the position of these locating means at all times.

In the utilization of the applicant's tool, the acetabulum is prepared as previously described. Two location holes 38,38 are fist drilled in the bottom of the cavity. The handle 70 is rotated in a counterclockwise direction to bring the cutting tool bit 48 to its outermost position. The surgeon then places the head of the tool into the patient's cavity and inserts the locating pins 36,36 in the holes 38,38. An assistant surgeon maintains a steady pressure on the handle 32 of the tool to maintain the pins in the holes and the tool in a fixed attitude. Since the cutting head 24 of the tool closely fits the patient's acetabular cavity the insertion of the tool into the cavity puts the cutting tool bit 48 in a position to start cutting a thread in the wall of the cavity. To this end the surgeon rotates the handle 30 which rotates the drive shaft 28, cutting tool bit 48 and cutting head 24. As the drive shaft and cutting tool rotate the cutting tool bit 48 is also advanced and moves longitudinally in the slot 46. At the same time the spring 58 keeps the tool carrier 50 outwardly displaced against the interior surface of the cutter head 24 on either side of the slot 46 so that the cutting tool bit 48 follows the contours of the prepared acetabular cavity while the threads are being cut. Rotation of the cutting head 24 occurs around the alignment disk 34 on the end of the central shaft 26. In this way, the surgeon cuts a spiral screw thread in the cortical wall of the acetabular cavity. Since only one thread is being cut at a time, the physical force required for the task is not excessive.

A modified form of the invention is shown in FIGS. 6-9. This form of the invention is very similar to the manually powered tool just described, but in the modified version the tool cutting bit is rotatably mounted in the cutting head and is powered by a compressed air motor. To accommodate the rotating track of the power-driven tool cutting bit, the slot 46 in the cutting head 24 is somewhat widened. Additionally, the registration of the tool carrier 50 relative to the cutting head 24 is controlled by cam-shaped grooves in the drive block 60 and this arrangement dispenses with the need for a biasing spring. The modified version of the invention improves the operation of the tool by eliminating the need for the surgeon to supply the thread-cutting force for the tool cutting bit. That force is now supplied by the compressed air motor and this simplifies the operation of the device for the surgeon.

As is best seen in FIG. 6, a small cylindrical compressed air motor 72 is fixedly attached to the drive shaft 28 by means of a clamp 74. The motor 72 is connected by a flexible hose 76 to a supply of compressed air (not shown) located off the cutting tool. A flexible drive shaft 78 is provided for the motor and this drive shaft, which is housed in a protective sheath 80, connects the motor 72 with a rotatable chuck 82 that passes through an opening in the end plate 64. The tool carrier 50 in this modified form of the invention is provided with a slot 84 in its outer periphery to accomodate the rotatble cutting tool bit 86. The tool bit 86 is fixed to a rotatable shaft 88 that passes tranvsersely across the slot 84 and the shaft 88 is fixed to the rotatable chuck 82. Because of its rotatable action, the cutting tool bit 86 is double ended with a cutting surface on each end and the slot 46 in the cutting head 24 is sufficiently wide to accomodate the rotatable track of the tool cutting bit. By reason of the connection of the shaft 88 with the rotatable chuck 82 the cutting tool bit 86 is rotated at high speed by the air motor 72 and serves to easily cut into the bony wall of the acetabulum.

In this modified form of the invention, the positioning of the tool carrier 50 relative to the cutting head 24 so that the tool cutting bit 86 is in a proper position to cut into the wall of the acetabulum, is controlled by matching cam-shaped grooves 90,90 cut into opposite sides of the drive block 60. These cam grooves 90,90 are curved in the same manner as the cutting head 24 and a pair of cam followers 92,92 set in the tool carrier 50 engage the grooves 90,90 and thereby cause the tool carrier 50 to move laterally in accord with the configuration of the grooves as the tool carrier 50 is advanced by the shaft 28. In this manner, the tool carrier 50 positions the tool cutting bit 86 enabling it to cut into the acetabulum.

As in the case of the manually operated tool, an assistant surgeon maintains steady pressure on the handle 32 to maintain the pins 36,36 in the holes 38,38 drilled in the bottom of the patient's acetabulum. The surgeon then rotates the handle 30 which, in turn, rotates shaft 28, the powered cutting bit tool 86 and the cutting head 24. The cutting tool bit 86, which rotates at high speed, cuts into the bony wall of the acetabulum with minimum manual effort. The cutting action of the bit no longer depends upon the manual rotation of the shaft 28 so the surgeon need only apply the amount of force required to keep the cutting tool bit 86 in contact with the uncut portion of the acetabulum wall. As is customary with air powered devices in the operating room, the control of the air motor is accomplished by means of a foot pedal (not shown) which the surgeon can operate with his foot while leaving both his hands free.

I claim:

1. A device for cutting threads in the wall of the acetabular cavity, said device comprising:
    (a) a rotatable cutting head shaped to substantially conform to the shape and size of the acetabular cavity and having a longitudinal opening therein,
    (b) a cutting tool located within the cutting head and having a rotatable cutting tool bit extending exteriorly of said cutting head through the opening,
    (c) power means for rotating said cutting tool bit, and
    (d) means for driving the cutting tool bit in a spiral path so as to cut threads in the wall of the acetabular cavity.

2. A thread-cutting device as set forth in claim 1 wherein said driving means comprise means for rotating the cutting head while simultaneously advancing the cutting tool bit in said longitudinal opening.

3. A thread-cutting device as set forth in claim 2 having means for positioning the cutting head relative to the acetabular cavity and the cutting head is carried by the positioning means and is rotatable relative thereto.

4. A thread-cutting device as set forth in claim 3 wherein the positioning means are mounted on a central shaft and the driving means comprise a drive shaft surrounding the central shaft and rotatable relative thereto.

5. A thread-cutting device as set forth in claim 4 wherein the central shaft is provided with a lead screw and the drive shaft with screw thead followers whereby relative rotation of the drive shaft and the central shaft rotates the cutting head and simultaneously advances the cutting tool bit in the longitudinal opening.

6. A thread-cutting device as set forth in claim 5 wherein said cutting tool bit is mounted in a tool carrier and the position of the tool carrier is guided by a control cam in the cutting head.

* * * * *